United States Patent
Takemoto et al.

(10) Patent No.: US 10,575,813 B2
(45) Date of Patent: Mar. 3, 2020

(54) MOVING TYPE RADIATION DEVICE

(71) Applicant: Shimadzu Corporation, Kyoto (JP)

(72) Inventors: Hajime Takemoto, Kyoto (JP); Toru Hayakawa, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 57 days.

(21) Appl. No.: 16/081,266

(22) PCT Filed: Mar. 1, 2016

(86) PCT No.: PCT/JP2016/056297
§ 371 (c)(1),
(2) Date: Aug. 30, 2018

(87) PCT Pub. No.: WO2017/149673
PCT Pub. Date: Sep. 8, 2017

(65) Prior Publication Data
US 2019/0069872 A1    Mar. 7, 2019

(51) Int. Cl.
*H05G 1/02*     (2006.01)
*A61B 6/00*     (2006.01)

(52) U.S. Cl.
CPC ............ *A61B 6/588* (2013.01); *A61B 6/4405* (2013.01); *A61B 6/447* (2013.01); *H05G 1/02* (2013.01)

(58) Field of Classification Search
CPC ....... A61B 6/588; A61B 6/447; A61B 6/4405; H05G 1/02
See application file for complete search history.

(56) References Cited

U.S. PATENT DOCUMENTS 5,283,823 A * 2/1994 Morris ................. A61B 6/4405
378/193
RE47,581 E * 8/2019 Moreno Vallejo ... A61B 6/4405
(Continued)

FOREIGN PATENT DOCUMENTS

JP         2013-523397 A        6/2013

OTHER PUBLICATIONS

International Search Report dated May 31, 2016 for PCT application PCT/JP2016/056297.
(Continued)

*Primary Examiner* — Kiho Kim
(74) *Attorney, Agent, or Firm* — Muir Patent Law, PLLC

(57) ABSTRACT

The present invention provides a moving type radiation device improved in usability. The stroke of an intermediate member in a conventional configuration can be increased when an effective diameter of a pinion with respect to an effective diameter of a lower sprocket is determined so that a magnitude of a relative movement that occurs when a lower sprocket and the pinion between an X-ray tube and the intermediate member becomes larger than the magnitude of the relative movement between the X-ray tube and the intermediate member. In the device according to the present invention, the intermediate member moves further toward the floor side than in a conventional device. The operator can move the device while feeling high operability in a state in which the visibility is not interrupted by the intermediate member.

3 Claims, 10 Drawing Sheets

(56) References Cited

U.S. PATENT DOCUMENTS

| | | | |
|---|---|---|---|
| 2010/0091942 A1* | 4/2010 | Pohjoispuro | A61B 6/14 378/38 |
| 2011/0249804 A1 | 10/2011 | Wendlandt et al. | |
| 2011/0249805 A1* | 10/2011 | Kralles | A61B 6/4405 378/198 |
| 2011/0249807 A1 | 10/2011 | Dirisio et al. | |
| 2012/0224673 A1* | 9/2012 | Barker | A61B 6/4405 378/198 |
| 2014/0098942 A1* | 4/2014 | Omura | A61B 6/4405 378/197 |
| 2014/0098943 A1* | 4/2014 | Omura | A61B 6/4452 378/198 |
| 2014/0133627 A1* | 5/2014 | Sakuragi | A61B 6/4429 378/62 |
| 2016/0015342 A1* | 1/2016 | Okuno | A61B 6/447 378/62 |
| 2017/0303882 A1* | 10/2017 | Ficarra | A61B 6/102 |
| 2018/0242933 A1* | 8/2018 | Sanbuichi | A61B 6/00 |
| 2019/0357863 A1* | 11/2019 | Dirisio | A61B 6/4405 |

OTHER PUBLICATIONS

Written Opinion of the International Searching Authority dated May 31, 2016 for PCT application PCT/JP2016/056297.

* cited by examiner

MOVING TYPE RADIATION DEVICE

TECHNICAL FIELD

The present invention relates to a moving type radiation device used for rounds for patients, and more particularly to a moving type radiation imaging device equipped with a mechanism for adjusting a height of a radiation source.

BACKGROUND ART

FIG. 13 illustrates a conventionally configured moving type radiation device. In this device, a radiation source 56 configured to irradiate radiation and a support column 52 supporting the radiation source 56 and extending in a vertical direction are provided on a hand-truck carriage. The support column 52 slidably supports the radiation source 56. The radiation source 56 is configured to be moved in the vertical direction while being supported by the support column 52. Such a device is electrically assisted, and is devised so that the operator can move easily without applying a strong force by hands.

Such a moving type radiation device can be moved to a subject's room. By using this device, it becomes possible to perform radiation imaging of the subject without moving the subject as much as possible.

FIG. 14 illustrates a mechanism for raising and lowering the radiation source 56. As shown on the left side of FIG. 14, the radiation source 56 is supported by a mechanism composed of a tip support column 54, an intermediate member 53, and a support column 52 connected with each other. When a force is applied so as to move the radiation source 56 upward and downward, the tip support column 54, the intermediate member 53, and the support column 52 move upward and downward in conjunction with the force.

One example for realizing such movement is a so-called well bucket type mechanism shown on the left side of FIG. 14 which is composed of a fixed pulley provided in the intermediate member 53. When the radiation source 56 is tried to move downward, the fixed pulley rotates counter-clockwise, and the wire is wound up to the left side. As a result, the radiation source 56 moves downward. The intermediate member 53 itself also moves downward while being differentiated from the radiation source 56 although the moving speed is not as fast as that of the radiation source 56. Hereinafter, this moving speed will be addressed.

The right side of FIG. 14 illustrates a diagram used for considering how fast the radiation source 56 and the intermediate member 53 move when the radiation source 56 is moved downward. When the radiation source 56 is moved downward, the radiation source 56 and the intermediate member 53 move relatively. It is assumed that the speed at this time is, for example, 0.1 m/s. The wire is wound up to the left side of the fixed pulley at this speed.

When the radiation source 56 is moved downward, the intermediate member 53 and the support column 52 move relatively. The speed at this time is 0.1 m/s. This is because that the wire will be wound up from the right side of the fixed pulley at this speed. That is, the radiation source 56 moves downward at the speed of 0.2 m/s with reference to the support column 52. That is, according to this mechanism, as shown in FIG. 15, the radiation source 56 moves at twice the speed of the intermediate member 53.

PRIOR ART

Patent Document

Patent Document 1: Japanese Translation of PCT International Application Publication No. 2013-523397

SUMMARY OF THE INVENTION

Problems to be Solved by the Invention

However, the conventionally configured moving type radiation device has the following problems.

That is, the conventionally configured moving type radiation device has a problem in that the usability is poor when moving the device.

FIG. 16 shows the positions of the radiation source 56, the support column 52, and the intermediate member 53 in a state in which the device is being moved by being pushed with hands (hereinafter referred to as conveyance state). Paying attention to the position of the intermediate member 53 at this time, it can be seen that the upper end of the intermediate member 53 is positioned slightly above the upper end of the support column 52. This causes inconvenience. In this state, it is assumed that the operator tries to push the device. Those entering the line of sight of the operator moving the device are the support column 52 and the intermediate member 53. The present invention focuses on the intermediate member 53 among them. If the intermediate member 53 is moved downward as shown by the dotted line in FIG. 16 so that the intermediate member 53 does not enter the line of sight as much as possible, the blind spot caused by the intermediate member 53 shown by the hatched portion in FIG. 16 disappears. Therefore, the field of view of the operator can be further opened to thereby improve the usability of the device.

However, the position of the tip of the intermediate member 53 cannot be freely changed. The left side of FIG. 14 shows a state in which the radiation source 56 has been moved to the uppermost position. Since the upper end of the intermediate member 53 at this time needs to assuredly support the radiation source 56 that has been moved to the uppermost position, the upper end must be set at a reasonably high position. If the upper end of the intermediate member 53 is lowered, the radiation source 56 will not be moved to the high position required for performance. It is assumed that the radiation source 56 which has been moved to the uppermost position as shown on the left side of FIG. 14 is moved to the lowermost position as shown in FIG. 16. It is assumed that the tip of the intermediate member 53 on the left side of FIG. 14 is positioned at a predetermined position. Assuming that the radiation source 56 is moved to the lowermost position from this state, the speed of the intermediate member 53 at this time is fixed to half of the moving speed of the radiation source 56 as shown in FIG. 15. Therefore, even if the radiation source 56 is moved to the lowermost position, the intermediate member 53 can move only half of the moving distance of the radiation source 56. The intermediate member 53 cannot be moved downward beyond this position.

In other words, the height of the intermediate member 53 when the radiation source 56 has been moved to the lowermost position is not freely designable but is uniquely determined by the performance required of the device.

Considering the device configuration that the radiation source 56 is moved upward and downward from a predetermined upper end to a predetermined lower end, the height of the intermediate member 53 when the radiation source 56 is in a carrying state is also uniquely determined. After all, even if the tip of the intermediate member 53 is obtrusive at this time, there is no way to improve by the conventional configuration.

The present invention has been made in view of the aforementioned problem, and the purpose is to provide a moving type radiation device improved in usability.

Means for Solving the Problems

The present invention has the following configuration to solve the above-mentioned problem.

The moving type radiation device according to the present invention includes:

a radiation source configured to irradiate radiation;

a support column extending in a vertical direction, wherein the support column vertically movably supports the radiation source;

an intermediate member provided at a position sandwiched between the radiation source and the support column and configured to move upward and downward in accordance with a lifting and lowering movement of the radiation source;

a support column inner wire having one end connected to the intermediate member and the other end connected to an inside of the support column;

a support column inner pulley configured to support the support column inner wire and serve as a fixed pulley for the support column provided in the support column;

a relay pulley provided on the other end side of the support column inner wire when viewed from the support column inner pulley and configured to support the support column inner wire and serve as a fixed pulley for the support column provided in the support column;

a spring mechanism configured to give tension to the support column inner wire and provided in the support column;

an upper sprocket rotatably provided at an upper portion of the intermediate member;

a lower sprocket rotatably provided at a lower portion of the intermediate member;

a roller chain meshed with the upper sprocket and the lower sprocket and coupled to the radiation source;

a pinion sharing a rotation shaft with the lower sprocket and rotatably provided to the intermediate member in a state in which a positional relationship thereof is fixed; and a rack meshed with the pinion and is provided to the support column so as to extend in a vertical direction, wherein an effective diameter of the lower sprocket is smaller than an effective diameter of the pinion.

[Functions and Effects] According to the present invention, it is possible to provide a moving type radiation device improved in usability. When the effective diameter of the pinion with respect to the effective diameter of the lower sprocket has been determined so that the magnitude of the relative movement between the intermediate member and the support column that occurs when the lower sprocket and the pinion are rotated becomes larger than the magnitude of the relative movement between the radiation source and the intermediate member, the stroke of the intermediate member in a conventional configuration can be increased. In other words, when the radiation source positioned at the uppermost position is moved to the lowermost position, the intermediate member is moved accordingly. According to a conventional configuration, the moving distance of the intermediate member at this time is determined to be half of the moving distance of the radiation source. However, according to the present invention, the intermediate member can be moved a longer distance.

Since there is such a difference, for the operator moving the radiation source downward, the operator feels that the intermediate member of the device according to the present invention will retract more quickly towards the floor than an intermediate member according to a conventional device. In the device according to the present invention, the intermediate member moves toward the floor side more than a conventional device. The operator can move the device while feeling high operability in a state in which the visibility is not interrupted by the intermediate member.

Further, in the moving type radiation device described above, it is more preferable that the upper sprocket have the same effective diameter as an effective diameter of the lower sprocket.

[Functions and Effects] The aforementioned configuration more specifically shows the device of the present invention. In the upper sprocket and the lower sprocket, when the diameters are determined so that the upper sprocket and the lower sprocket rotate at the same rotation speed, the configuration of the present invention can be more reliably realized.

Further, in the moving type radiation device described above, it is more preferable that the support column inner wire be multiplexed.

[Functions and Effects] The aforementioned configuration more specifically shows the device of the present invention. When the support column inner wire is multiplexed, a device better in safety can be provided.

Effects of the Invention

According to the present invention, it is possible to provide a moving type radiation device improved in usability. When the effective diameter of the pinion with respect to the effective diameter of the lower sprocket has been determined so that the magnitude of the relative movement between the intermediate member and the support column that occurs when the lower sprocket and the pinion are rotated becomes larger than the magnitude of the relative movement between the X-ray tube and the intermediate member, the stroke of the intermediate member in a conventional configuration can be increased. In the device according to the present invention, the intermediate member moves further toward the floor side than in a conventional device. The operator can move the device while feeling high operability in a state in which the visibility is not interrupted by the intermediate member.

EMBODIMENTS FOR CARRYING OUT THE INVENTION

Subsequently, a moving type radiation device according to the present invention will be described. The device according to the present invention is a radiation device capable of carrying to a patient's room by traveling a corridor of a hospital. By combining this device with a radiation detector, it is possible to capture a radiation image of a subject even in a patient's room. X-rays correspond to the radiation of the present invention.

Example 1

Figure 1:
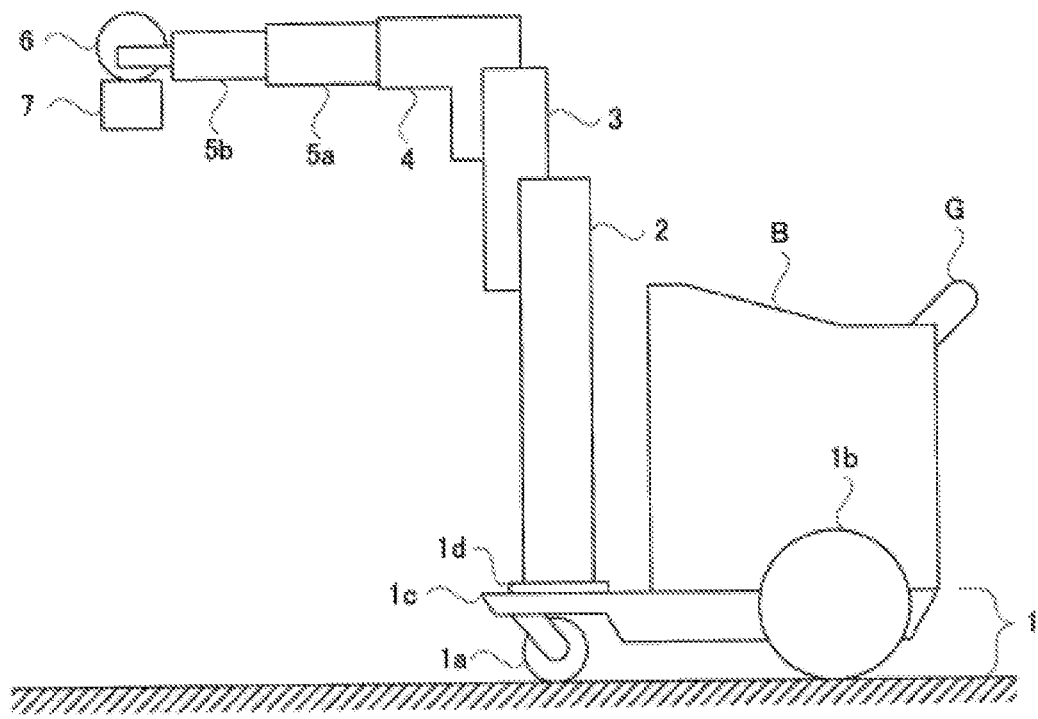
FIG. 1 is a schematic diagram illustrating the entire configuration of a moving type X-ray device according to Example 1.

FIG. 1 shows an overall configuration of a moving type X-ray device according to the present invention. The device according to the present invention is equipped with a chassis 1 at the base portion of the device. The chassis 1 has a base 1c provided with two front wheels 1a and two rear wheels 1b. The chassis 1 is mounting other parts constituting the device. The chassis 1 is configured to support a support column 2. The chassis 1 is provided with two front wheels and two rear wheels.

A main body B is mounted on the chassis 1. The main body B is provided with a power supply device, a battery, an operation panel, a holder for housing a radiation detector, and the like. The main body B is provided with a grip G that an operator holds when moving the device. It is configured such that when an operator applies a force to the grip G, an assist function provided in the chassis 1 works to assist the force given by the operator. As a result, an operator can lightly move the device.

A support column 2 is a member extending in the vertical direction, and the inside is hollow. This support column 2 is rotatable about the central axis extending in the vertical direction.

The intermediate member 3 is a vertically elongated member provided so as to extend the support column 2. The support column 2 movably supports the intermediate member 3 downward and upward. The support column 2 is provided with a groove extending in the vertical direction configured to receive the intermediate member 3, and the intermediate member 3 can move in the vertical direction along this groove. The intermediate member 3 is provided at a position between the X-ray tube 6 and the support column 2 and moves upward and downward in accordance with the upward and downward movement of the X-ray tube 6.

A tip support column 4 is an L-shaped member provided so as to further extend the intermediate member 3. The intermediate member 3 supports the tip support column 4 in an upwardly and downwardly movable manner. The tip support column 4 is composed of two arms orthogonal to each other, one arm extending in the vertical direction and the other arm extending in the horizontal direction. The intermediate member 3 is provided with a groove extending in the vertical direction configured to receive the vertical direction arm possessed by the tip support column 4, and the tip support column 4 can move in the vertical direction along this groove.

Figure 2:
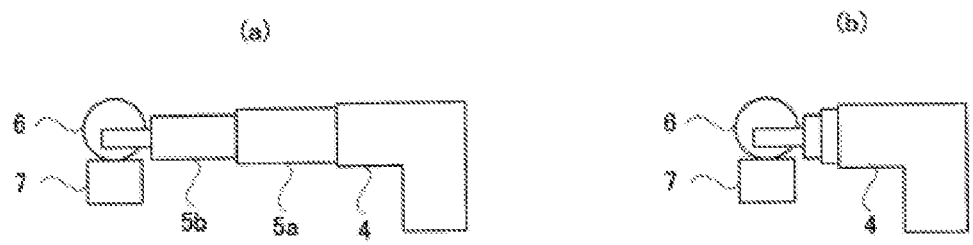
FIG. 2 is a schematic view for explaining a tip support column according to Example 1.

Lateral support columns 5a and 5b are horizontally elongated members extending in the horizontal direction. Three members including the horizontal arm, the lateral support column 5a, and the lateral support column 5b possessed by the tip support column 4 constitute a nest type expansion structure. The left side of FIG. 2 shows the state in which the expansion structure is fully extended. The right side of FIG. 2 shows the state in which the expansion structure is fully contracted. This expansion structure can be operated manually.

The X-ray tube 6 is an apparatus for generating X-rays. The X-ray tube 6 is a load object and has a considerable weight. The X-ray tube 6 is supported by the lateral support column 5b. The support column 2, the intermediate member 3, the tip support column 4, the lateral support columns 5a and 5b are configured to transmit the load of the X-ray tube 6 to the chassis 1. The circuit related to the control of the X-ray tube 6 is housed in the main body B. To the X-ray tube 6, a collimator 7 for restricting the spread of X-rays is attached. This collimator 7 moves following the movement of the X-ray tube 6. The X-ray tube 6 irradiates X-rays.

Figure 3:
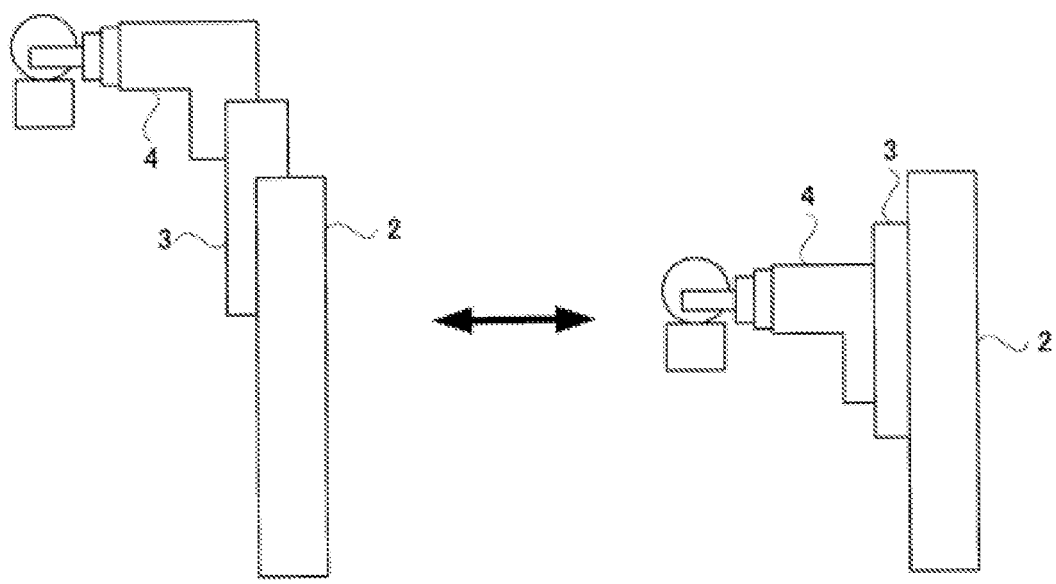
FIG. 3 is a schematic view for explaining a vertical movement of the X-ray tube according to Example 1.

FIG. 3 illustrates the lifting and lowering movement of the tip support column 4. The left side of FIG. 3 illustrates a state in which the tip support column 4 is moved to the uppermost position, and the right side of FIG. 3 illustrates a state in which the tip support column 4 is moved to the lowermost position. When the tip support column 4 is moved in the vertical direction, the intermediate member 3 moves in conjunction with this. That is, it is configured such that when the tip support column 4 is moved in one direction by a certain movement amount, the intermediate member 3 is moved in the same direction at a fixed ratio of the movement amount.

Thus, according to the apparatus of the present invention, it is configured such that the vertical movements of the X-ray tube 6 are served by the mechanism composed of the support column 2, the intermediate member 3 and that the lateral movements of the X-ray tube 6 are served by the tip support column 4, the lateral support column 5a, and the lateral support column 5b. Note that the rotational movements of the X-ray tube 6 are served by a rotation base 1d. When a force that rotates the X-ray tube 6 about the vertical axis is applied, the support column 2 rotates with respect to the chassis 1. Then, the intermediate member 3, the tip support column 4, the lateral support columns 5a and 5b, and the X-ray tube 6 rotate so as to follow the support column 2 while keeping the positional relationship with the support column 2.

The support column 2 is hollow, and is provided with various mechanisms in the inner hollow space of the support column 2. On the inner surface corresponding to the ceiling of the internal space of the support column, there is provided a fixing tool for fixing a tip of a wire. Similarly, the intermediate member 3 is also provided with a fixing tool.

In the support column, a winding pulley 14a and a spiral pulley 14b are provided. These pulleys 14a and 14b are fixed pulleys for the support column 2 and share the rotation shaft. The winding pulley 14a has a cylindrical shape, and is provided with a coiled groove. On the other hand, the spiral pulley 14b is a pulley having a wheel shaft whose radius ratio is variable, and has a tapered shape. The winding pulley 14a and the spiral pulley 14b are each provided with a fixing tool for fixing a tip of a wire.

A winding pulley wire 12a has one end fixed to the fixing tool of the intermediate member 3 and the other end fixed to the fixing tool of the winding pulley 14a. The winding pulley wire 12a is held in the form wound around the winding pulley 14a. Therefore, the winding pulley wire 12a extends from the winding pulley 14a as a starting point and is held so as to unwind toward the lower side of the winding pulley 14a.

A support column inner wire 12b has one end fixed to the fixing tool of the spiral pulley 14b and the other end fixed to the fixing tool provided in the support column 2. The support column inner wire 12b is held in the form wound around the spiral pulley 14b. Therefore, the support column inner wire 12b extends from the spiral pulley 14b as a starting point and is held so as to unwind toward the lower side of the spiral pulley 14b.

Inside the support column 2, between the support column inner pulley 14 and the fixing tool provided on the inner surface of the support column 2, a relay pulley 13a which is a fixed pulley for the support column 2 is provided. The relay pulley 13a supports the support column inner wire 12b. The support column inner wire 12b is held in a state of being wound on the relay pulley 13a so as to be in contact with the upper side of the relay pulley 13a. The relay pulley 13a is provided on the other end side of the support column inner wire 12b when viewed from the support column inner pulley 14 and is configured to support the support column inner wire 12b and serves as a fixed pulley for the support column 2 provided in the support column 2.

On each side of the relay pulley 13a, a movable pulley 13b is provided which moves with respect to the relay pulley 13a. The support column inner wire 12b is held in a state of being wound on the two movable pulleys 13b so as to be in contact with the lower side of the two movable pulleys 13b.

Therefore, starting from the fixing tool of the intermediate member 3, the support column inner wire 12b is wound on the support column inner pulley 14, the movable pulley 13b, the relay pulley 13a, and the movable pulley 13b one after another, and extends to the end point of the fixing tool provided on the inner surface of the support column 2.

<Arrangement Example of Mechanism>

Figure 4:
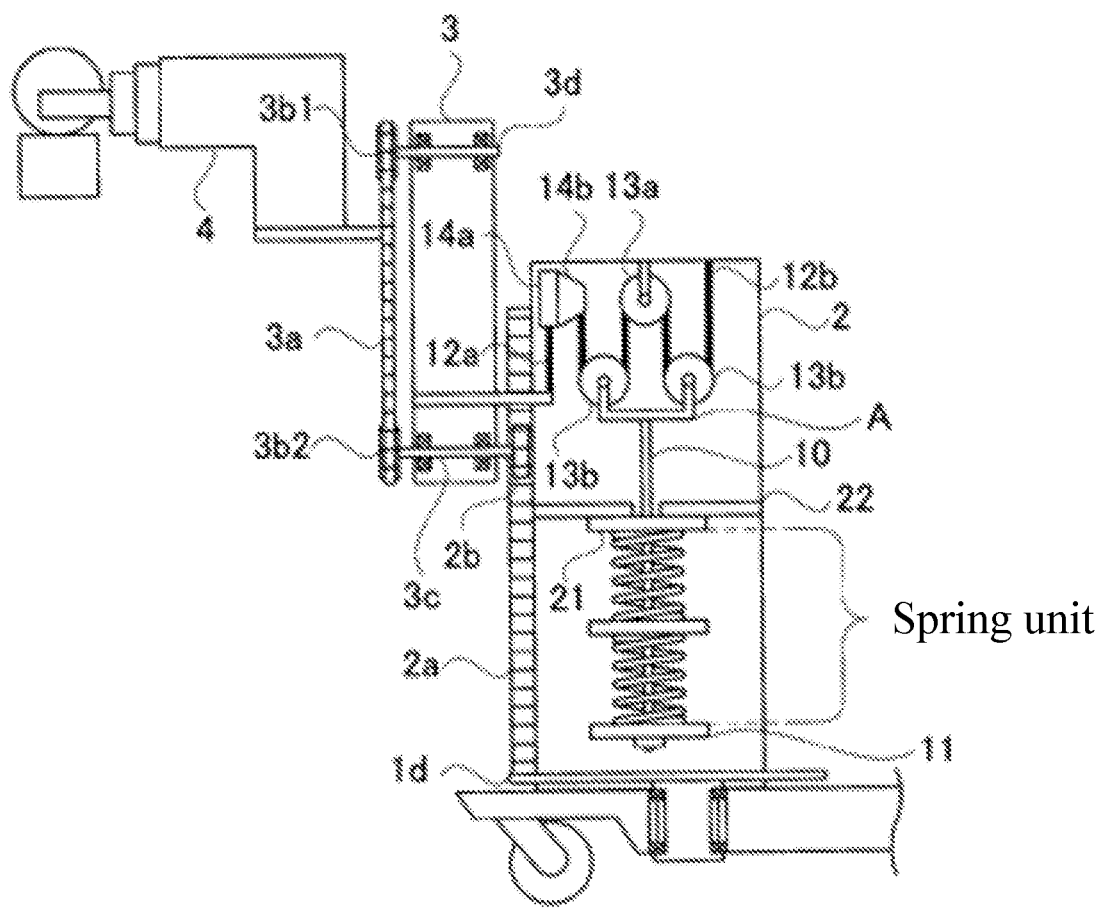
FIG. 4 is a schematic view for explaining a mechanism for realizing the vertical movement of the X-ray tube according to Example 1.
Figure 5:
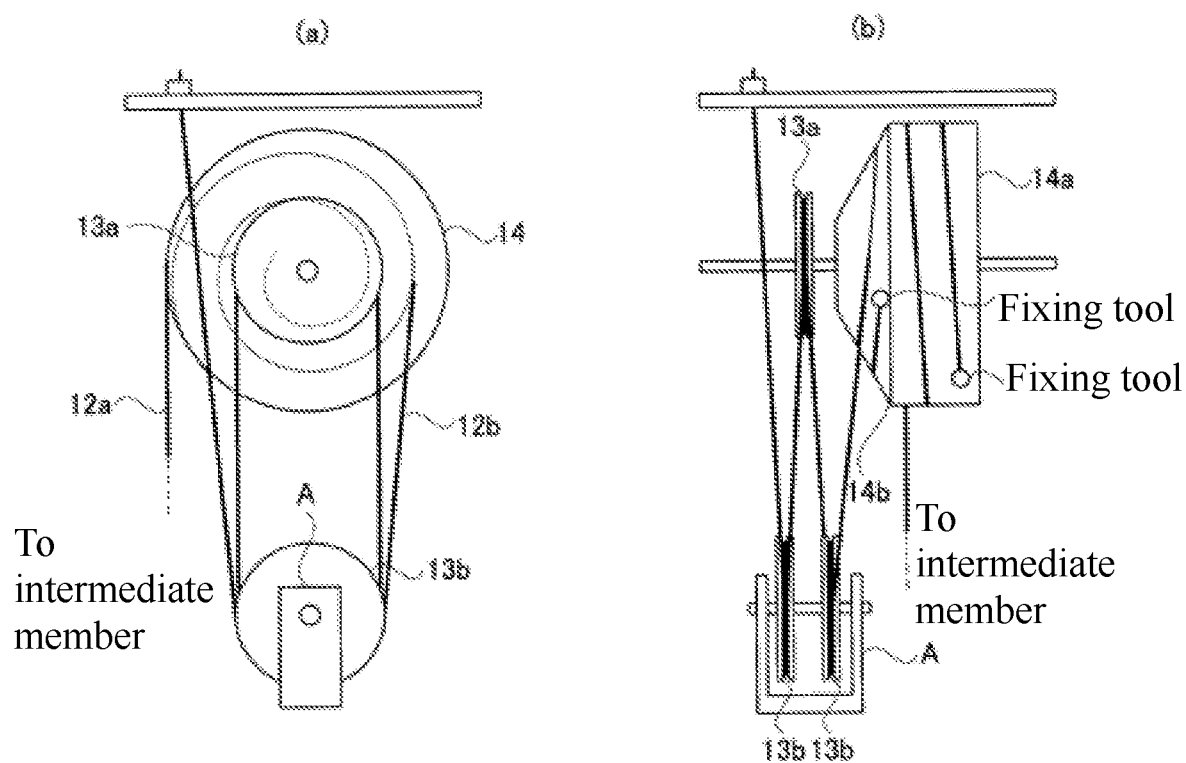
FIG. 5 is a schematic diagram for explaining an implementation example of the mechanism according to Example 1.

The inside of the support column 2 shown in FIG. 4 is illustrated so that the transmission of power can be easy to understand. If the internal mechanism of the support column 2 is configured as shown in FIG. 4, the diameter of the support column 2 has to be made considerably large. On the other hand, FIG. 5 shows an arrangement example in which the same mechanism as in FIG. 4 is arranged in a more compact manner. According to such an arrangement example, it is possible to reduce the diameter of the support column 2.

The left side of FIG. 5 shows the arrangement example as viewed from the rotational axis direction of the support column inner pulley 14. According to the explanation with reference to FIG. 4, the rotation shaft of the support column inner pulley 14 is depicted so as to be orthogonal to the rotation shaft of the relay pulley 13a, but the rotation axes of the support column inner pulley 14 and the relay pulley 13a may be made to coincide with each other as shown on the left side of FIG. 5. Further, according to the explanation with reference to FIG. 4, the movable pulley 13b is arranged in a direction orthogonal to the rotation shaft, but both the rotation axes may be arranged so as to coincide with each other as shown on the left side of FIG. 5. The right side of FIG. 5 shows the arrangement example as viewed from the direction orthogonal to the rotation shaft of the support column inner pulley 14.

<Spring Mechanism>

The spring mechanism generates a force to unwind the support column inner wire 12b from the spiral pulley 14b by pulling the support column inner wire 12b downward via the two movable pulleys 13b. This force detains the downward movement of the intermediate member 3. The spring mechanism is a configuration that gives a tension to the support column inner wire 12b, and is provided in the support column 2.

<Features of Present Invention>

The feature of the present invention resides in the mechanism for moving the intermediate member 3. In FIG. 4, a rack 2a and a pinion 2b are illustrated. The rack 2a is a vertically extending member fixed to the support column 2. The pinion 2b is meshed with the rack 2a and fixed to one end of the rotation shaft 3c provided at the lower end of the intermediate member 3. The pinion 2b is rotatably supported to the intermediate member 3 via the rotation shaft 3c. When the intermediate member 3 moves relative to the support column 2, the pinion 2b moves on the rack 2a, so the rotation shaft 3c will rotate accordingly. Assuming that the relative movement of the intermediate member 3 with respect to the support column 2 is constant, the rotation shaft 3c will rotate at a constant speed. The rack 2a is meshed with the pinion 2b which shares the rotation shaft with the sprocket 3b2 and is rotatably provided on the intermediate member 3 in a state in which their positional relationships are fixed, and extends in the vertical direction.

Also, in FIG. 4, a roller chain 3a and sprockets 3b1 and 3b2 are illustrated. The roller chain 3a is fixed to the tip support column 4 via a fixing tool. The two sprockets 3b1 and 3b2 are rotatably mounted on the intermediate member 3. One sprocket 3b1 is positioned at the upper end of the intermediate member 3, and the other sprocket 3b2 is positioned at the lower end of the intermediate member 3. These two sprocket 3b1 and 3b2 have the same diameter. The roller chain 3a is meshed with the sprocket 3b1 and the sprocket 3b2 and is coupled to the X-ray tube 6 via the tip support column 4. When the roller chain 3a is driven, the tip support column 4 and the X-ray tube 6 move in the vertical direction in accordance with this driving. When the roller chain 3a is driven, the tip support column 4 and the X-ray tube 6 move in the vertical direction following this driving. In other words, the sprocket 3b1 has the same effective diameter as the effective diameter of the sprocket 3b2. Note that the sprocket 3b1 corresponds to the upper sprocket of the present invention and the sprocket 3b2 corresponds to the lower sprocket of the present invention.

Figure 6:
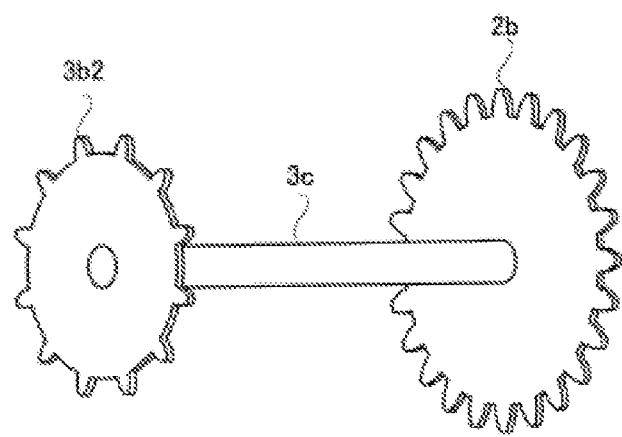
FIG. 6 is a schematic view for explaining a pinion and a lower sprocket according to Example 1.

The pinion 2b and the sprocket 3b2 share the same rotation shaft 3c, and therefore this point will be explained. FIG. 6 illustrates that the pinion 2b is fixed to one end of the rotation shaft 3c and the sprocket 3b2 is fixed to the other end thereof. The sprocket 3b2 is slightly smaller than the pinion 2b. That is, the effective diameter of the sprocket 3b2 is smaller than the effective diameter of the pinion 2b so that the magnitude of the relative movement between the intermediate member 3 and the support column 2 that occurs when the lower sprocket 3b2 and the pinion 2b are rotated becomes larger than the magnitude of the relative movement between the X-ray tube 6 and the intermediate member 3.

The operation of the mechanism composed of the tip support column 4, the intermediate member 3, and the support column 2 will be described. When an operator applies a force that pushes down the X-ray tube 6, the tip support column 4 moves following the X-ray tube 6, and the roller chain 3a is driven accordingly. Then, the sprockets 3b1 and 3b2 rotate according to this driving. The rotational force of the sprocket 3b2 is transmitted to the pinion 2b. When the roller chain 3a is driven, the tip support column 4 and the intermediate member 3 move relative to each other.

The fact that the sprocket 3b2 rotates means that the pinion 2b having the same rotation shaft also rotates. When the pinion 2b rotates, the intermediate member 3 and the support column 2 move relatively. That is, when a force pushing down the X-ray tube 6 is applied, the X-ray tube 6 is moved downward and the tip support column 4 follows the movement. The intermediate member 3 is moved downward at a speed slower than the speed of the X-ray tube 6 in conjunction with the movement of the X-ray tube 6.

The feature of the present invention resides in that the size of the pinion 2b and that of the sprocket 3b2 are different. Suppose the size of the pinion 2b and that of the sprocket 3b2 are exactly the same. At this time, when the rotation shaft 3c rotates one turn, the circumference of the pinion 2b and the circumference of the sprocket 3b2 are the same. When the rotation shaft 3c rotates one turn, the pinion 2b advances by a certain length on the rack 2a, and the sprocket 3b2 pulls in the roller chain 3a by a certain distance. Since the circumference of the pinion 2b and the circumference of the sprocket 3b2 are the same, the travel distance of the pinion 2b on the rack 2a and the pulled distance of the roller chain 3a become the same.

By changing the size of the pinion 2b and the size of the sprocket 3b2, it is possible to change the pulled distance of the roller chain 3a with respect to the travel distance of the pinion 2b on the rack 2a. This makes it possible to change the moving speed of the intermediate member 3 with respect to the moving speed of the X-ray tube 6, which has been conventionally unambiguous.

Figure 7:
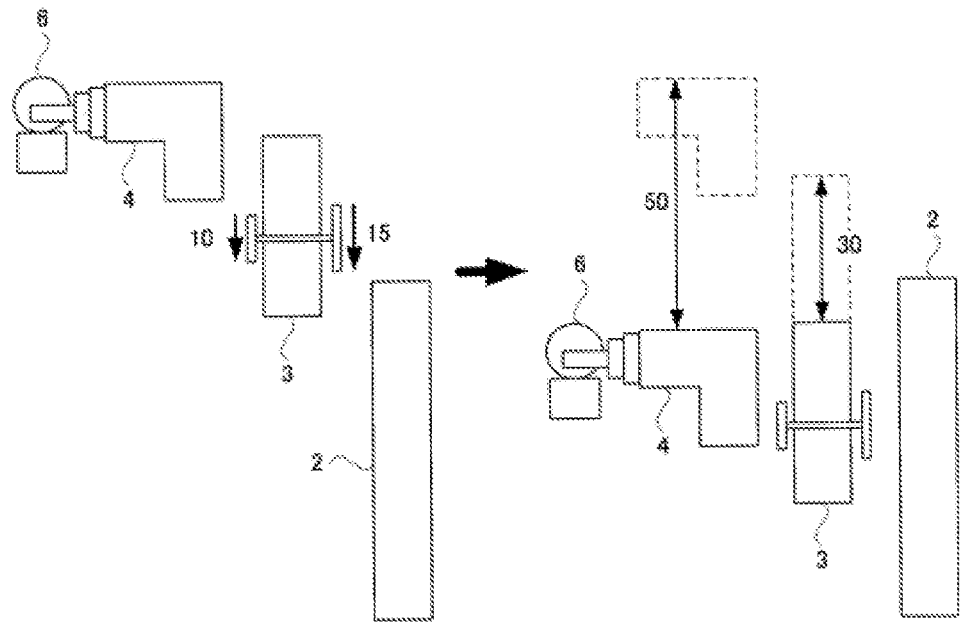
FIG. 7 is a schematic diagram for explaining a movement mode of an intermediate member according to Example 1.

This point will be described with reference to FIG. 7. FIG. 7 shows a case in which the circumference (the circumference based on the effective diameter) of the pinion 2b is 1.5 when the circumference (the circumference based on the effective diameter) of the sprocket 3b2 is 1. In this case, assuming that the relative movement between the tip support column 4 and the intermediate member 3 is 1 cm, the relative movement between the intermediate member 3 and the support column 2 is 1.5 times, i.e., 1.5 cm. That is, the relative movement that occurs between the intermediate member 3 and the support column 2 is greater than the relative movement that occurs between the tip support column 4 and the intermediate member 3. In other words, the travel distance of the pinion 2b on the rack 2a is larger than the pulled distance of the roller chain 3a in accordance with the rotation of the rotation shaft 3c.

FIG. 7 illustrates the movement of the intermediate member 3 under such conditions. The left side of FIG. 7 shows the state in which the X-ray tube 6 is positioned at the uppermost position. The right side of FIG. 7 shows the state in which the X-ray tube 6 is pressed downward by 50 cm from the aforementioned state. Looking at the breakdown of the movements, the X-ray tube 6 and the tip support column 4 are moved by 20 cm with respect to the intermediate member 3, and the intermediate member 3 is moved by 30 cm, i.e., 1.5 times 20 cm, with respect to the support column 2. The X-ray tube 6 is moved by 50 cm including the relative movement with respect to the support column 2.

Figure 8:
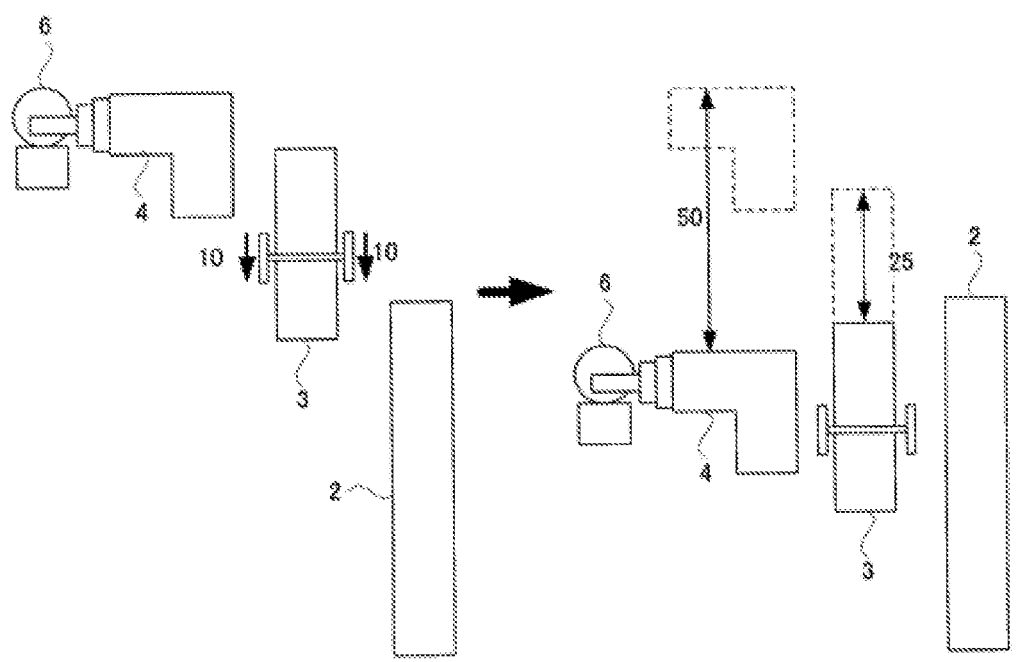
FIG. 8 is a schematic diagram for explaining a movement mode of the intermediate member according to Example 1.

On the other hand, FIG. 8 shows an apparatus similar to the apparatus shown in FIG. 1 in which the circumference of the pinion 2b and the circumference of the sprocket 3b2 are the same. This device exhibits the same behavior as the conventional movement of the intermediate member 3, so the behavior will be described. In this case, assuming that the relative movement between the tip support column 4 and the intermediate member 3 is 1 cm, the relative movement between the intermediate member 3 and the support column 2 becomes the same 1 cm. That is, the relative movement that occurs between the tip support column 4 and the intermediate member 3 and the relative movement that occurs between the intermediate member 3 and the support column 2 becomes the same. In other words, the pulled distance of the roller chain 3a in accordance with the rotation of the rotation shaft 3c and the travel distance of the pinion 2b on the rack 2a is the same.

FIG. 8 illustrates the movement of the intermediate member 3 under such conditions. The left side of FIG. 8 shows the state in which the X-ray tube 6 is positioned at the uppermost position. The right side of FIG. 8 shows the state in which the X-ray tube 6 is pressed downward by 50 cm from the aforementioned state. Looking at the breakdown of the movements, the X-ray tube 6 and the tip support column 4 are moved by 25 cm with respect to the intermediate member 3, and the intermediate member 3 is moved by the same 25 cm with respect to the support column 2. The X-ray tube 6 is moved by 50 cm including the relative movement with respect to the support column 2.

FIG. 7 shows a configuration according to the present invention, and FIG. 8 shows a configuration corresponding to a conventional device. In both the cases, the X-ray tube 6 positioned at the uppermost position was moved downward by 50 cm. The difference between these configurations is the position of the intermediate member 3 after the X-ray tube 6 has been moved downward by 50 cm. When the X-ray tube 6 was positioned at the uppermost position, the intermediate member 3 was also positioned at the uppermost position. There is no difference in the position of the intermediate member 3 between the device shown in FIG. 7 and the device shown in FIG. 8. However, the situation is different when attention is paid to the intermediate member 3. In the case of FIG. 7, the intermediate member 3 was moved by 30 cm from the uppermost position. On the other hand, in the case of FIG. 8, the intermediate member 3 was moved by 25 cm from the same start position. In other words, the intermediate member 3 was moved by 5 cm downward in the case of FIG. 7 than in the case of FIG. 8. In other words, the intermediate member 3 of the device of FIG. 7 moves faster than that of FIG. 8.

Figure 9:
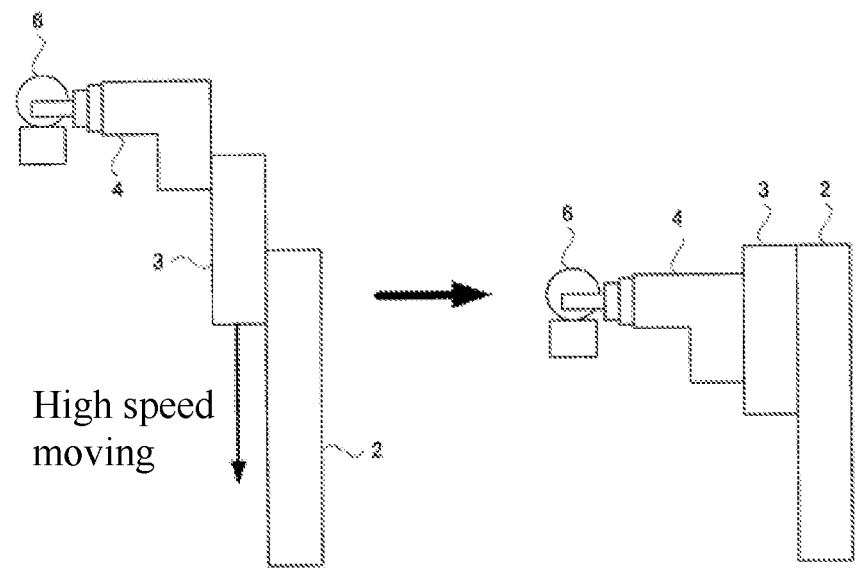
FIG. 9 is a schematic diagram for explaining the movement mode of the intermediate member according to Example 1.
Figure 10:
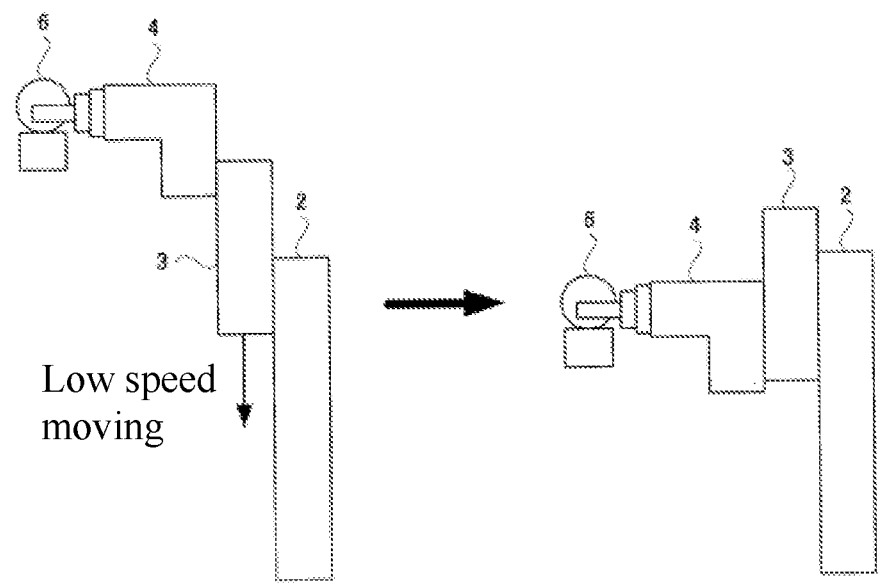
FIG. 10 is a schematic diagram for explaining the movement mode of the intermediate member according to Example 1.

The fast movement of the intermediate member 3 has the merit of clearing the operator's view of the device. FIG. 9 and FIG. 10 explain this merit. FIG. 9 shows a device according to the present invention having a device configuration in which the intermediate member 3 moves at a high speed. FIG. 10 shows a conventional device having device configuration in which the intermediate member 3 moves at a low speed. The left side of FIG. 9 and that of FIG. 10 each illustrate the case in which the X-ray tube 6 is positioned at the uppermost position. The positional relationship of the X-ray tube 6, the tip support column 4, the intermediate member 3, the support column 2 at this time is the same for both the devices.

The right side state of FIG. 9 and that of FIG. 10 each show a state in which the X-ray tube 6 is placed in a conveyance state from the left side state of FIG. 9 and that of FIG. 10. The position of the X-ray tube 6 at this time is the same between the device of FIG. 9 and the device of FIG. 10.

As described with reference to FIG. 7 and FIG. 8, the moving speed of the intermediate member 3 is different between these devices during the movement of the X-ray tube 6. The moving speed of the intermediate member 3 is faster in the device of FIG. 9 than in the device of FIG. 10. Accordingly, for the operator moving the X-ray tube 6 downward, the operator feels that the intermediate member 3 of the device of FIG. 9 will retract more quickly toward the floor than the intermediate member 3 of FIG. 10. In the device of FIG. 9, the intermediate member 3 moves toward the floor side more than the conventional device of FIG. 10. The operator can move the device with the grip G held while feeling high operability in a state in which the visibility is not interrupted by the intermediate member 3.

As described above, according to the present invention, it is possible to provide a moving type radiation device improved in usability. When the effective diameter of the pinion 2b with respect to the effective diameter of the sprocket 3b2 has been determined so that the magnitude of the relative movement between the intermediate member 3 and the support column 2 which occurs when the sprocket 3b2 and the pinion 2b are rotated becomes larger than the magnitude of the relative movement between the X-ray tube 6 and the intermediate member 3, the stroke of the intermediate member 3 in a conventional configuration can be increased. In other words, when the X-ray tube 6 positioned at the uppermost position is moved to the lowermost positioned, the intermediate member 3 is moved accordingly. According to a conventional configuration, the moving distance of the intermediate member 3 at this time is determined to be half of the moving distance of the X-ray tube 6. However, according to the present invention, the intermediate member 3 can be moved a longer distance.

The present invention is not limited to the aforementioned example, but can be modified as follows.

Figure 11:
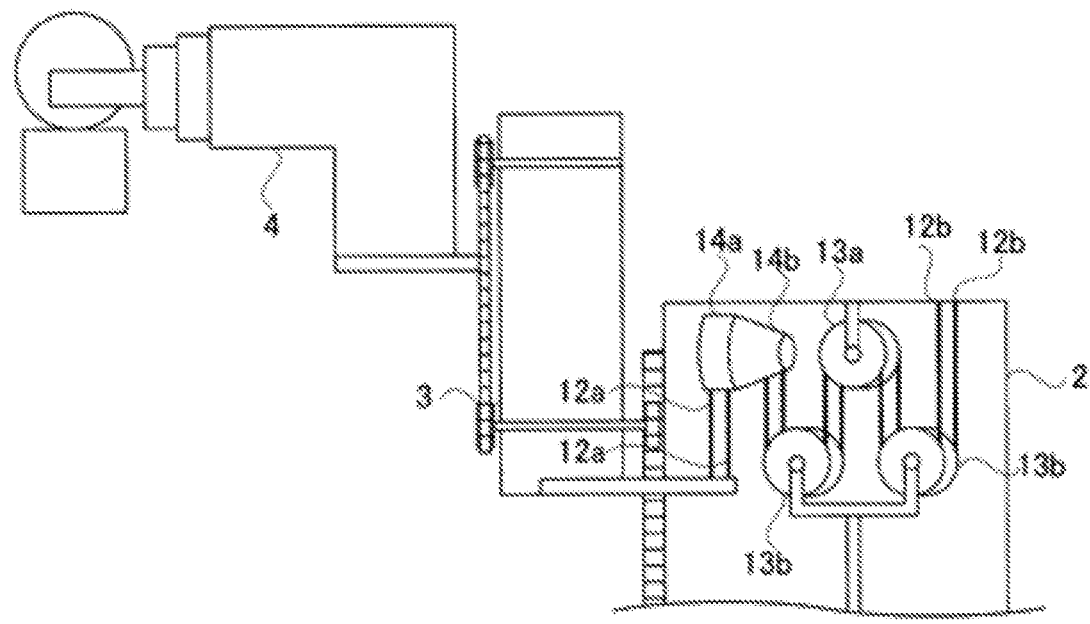
FIG. 11 is a schematic diagram for explaining one modified example according to the present invention.

(1) According to the above-described example, there are only one winding pulley wire 12a and only one support column inner wire 12b, but the configuration of the present invention is not limited thereto. As shown in FIG. 11, the winding pulley wire 12a and the support column inner wire 12b can be doubled. With such a configuration, even in cases where one of the winding pulley wire 12a and the support column inner wire 12b is broken, the remaining wire which is not broken can support the X-ray tube 6, which prevents dropping of the X-ray tube 6. Note that the winding pulley wire 12a and the support column inner wire 12b can be tripled or more.

(2) According to the aforementioned configuration, there are only one set of the sprocket and the roller chain in the device, but the sprocket and the roller chain may be configured to be multiple.

Figure 12:
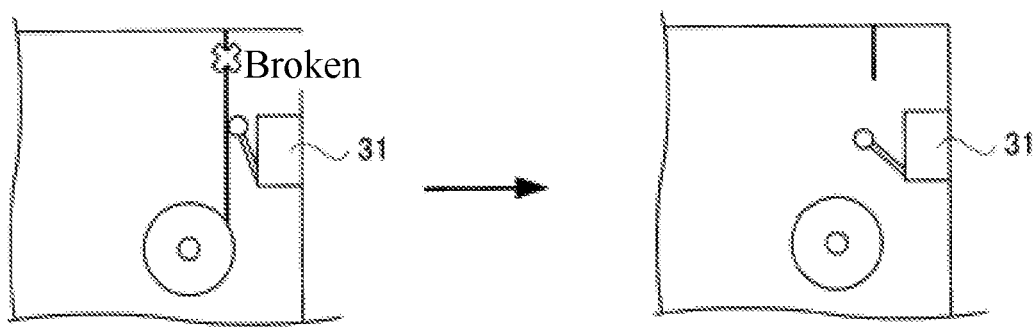
FIG. 12 is a schematic diagram for explaining one modified example according to the present invention.
Figure 13:
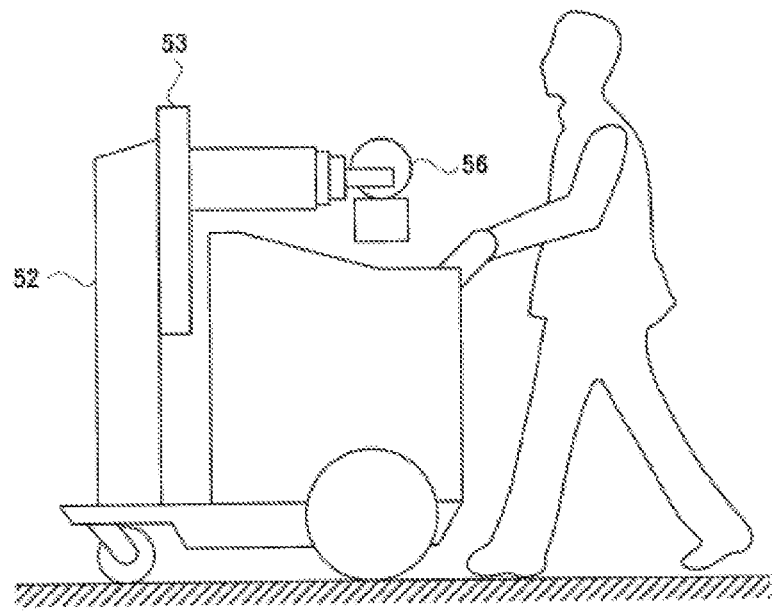
FIG. 13 is a conceptual diagram illustrating a moving type radiation device according to a conventional configuration.
Figure 14:
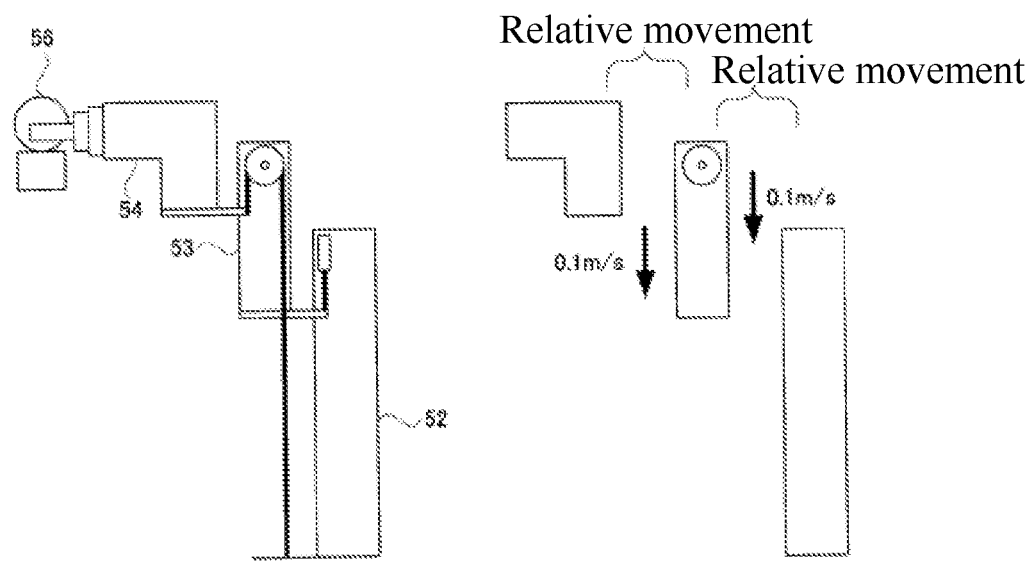
FIG. 14 is a schematic diagram for explaining the relative movement of each member constituting the moving type radiation device according to a conventional configuration.
Figure 15:
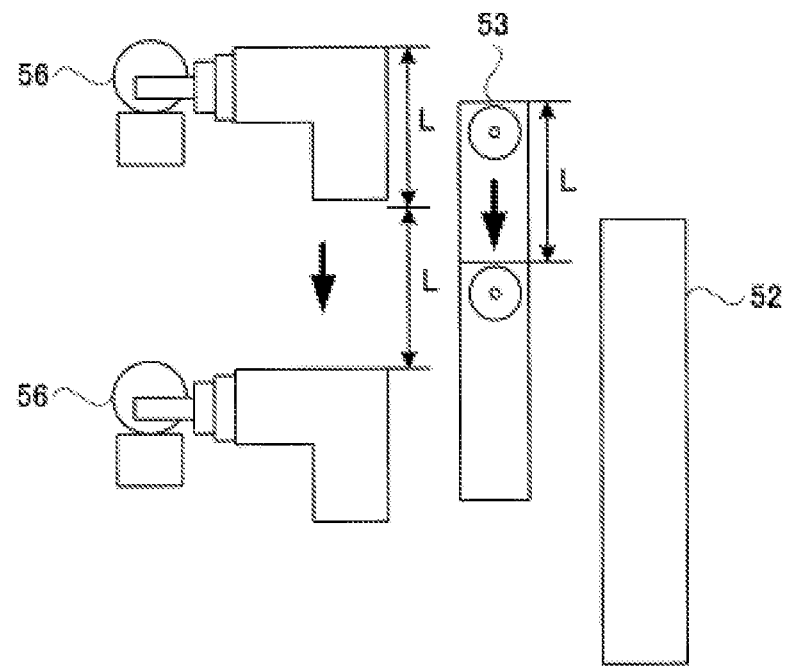
FIG. 15 is a schematic diagram for explaining the positional relationship of each member constituting a moving type radiation device according to a conventional configuration.
Figure 16:
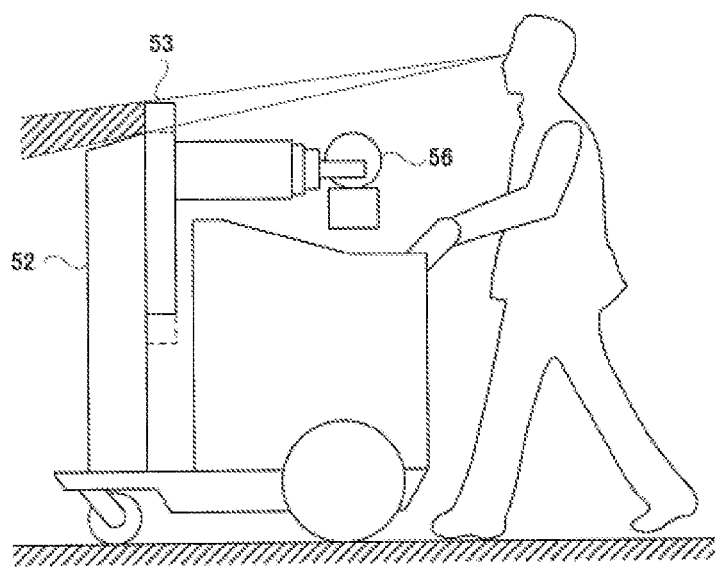
FIG. 16 is a schematic diagram for explaining the relative movement of each member constituting a moving type radiation device according to a conventional configuration.

(3) According to the above-described example, there is no description on a configuration for sensing the breakage of the support column inner wire 12b, but a sensor 31 for detecting the tension of the wire may be provided as shown in FIG. 12. The sensor 31 is provided with such an arm that is pushed down when a downward force is applied and is pushed up when the force is released. The sensor 31 is an electronic component that turns ON when the arm is pushed down, and turns OFF when the arm is raised. The sensor 31 is mounted in the support column 2 so that its arm is pressed against the support column inner wire 12b and is in the ON state when the arm is pushed down by the support column inner wire 12b. A spherical reinforcing member is provided at the tip of the arm of the sensor 31 to prevent wear of the arm of the sensor 31 by the support column inner wire 12b.

When the support column inner wire 12b is broken, the force pushing down the arm disappears, so the arm pushes itself up and the sensor 31 turns off. The moving type X-ray device executes an alarm at this point notifying the operator of the breakage of the wire based on the output of the sensor 31. Such a modified example is suitable for the configuration as shown in FIG. 11 in which wires are multiplexed. That is, with the configuration as shown in FIG. 11, even if one wire is broken, a normal operation can be performed by another wire. However, if it is left unattended, it may happen that the broken wire tangles and damages the structure inside the support column 2. Therefore, it is better to transmit the breakage of the wire to the operator as soon as possible. In cases where the wires are multiplexed as shown in FIG. 11, the sensor 31 is provided for each of the two support column inner wires 12b.

The sensor 31 of this modified example is an electronic component that turns ON when the arm is pushed down and turns OFF when the arm is pushed up. In place this, this modified example may be configured by using a sensor 31 that turns OFF when the arm is pushed down and turns ON when the arm is pushed up.

(4) According to the above-described configuration, the effective diameter of the sprocket 3b1 is the same as the effective diameter of the sprocket 3b2, but the present invention is not limited to this configuration. It may be configured such that the effective diameter of the sprocket 3b1 be made larger than the effective diameter of the sprocket 3b2 or the effective diameter of the sprocket 3b1 be made smaller than the effective diameter of sprocket 3b2.

DESCRIPTION OF REFERENCE SYMBOLS 2a rack
2b pinion
3a roller chain
3b1 sprocket (upper sprocket)
3b2 sprocket (lower sprocket)

INDUSTRIAL APPLICABILITY

As described above, the present invention is suitably used in a medical field.

The invention claimed is:
1. A moving type radiation device, comprising:
a radiation source configured to irradiate radiation;
a support column extending in a vertical direction, wherein the support column vertically movably supports the radiation source;
an intermediate member provided at a position sandwiched between the radiation source and the support column and configured to move upward and downward in accordance with a lifting and lowering movement of the radiation source;

a support column inner wire having one end connected to the intermediate member and the other end connected to an inside of the support column;

a support column inner pulley configured to support the support column inner wire and serve as a fixed pulley for the support column provided in the support column;

a relay pulley provided on the other end side of the support column inner wire when viewed from the support column inner pulley and configured to support the support column inner wire and serve as a fixed pulley for the support column provided in the support column;

a spring mechanism configured to give tension to the support column inner wire and provided in the support column;

an upper sprocket rotatably provided at an upper portion of the intermediate member;

a lower sprocket rotatably provided at a lower portion of the intermediate member;

a roller chain meshed with the upper sprocket and the lower sprocket and coupled to the radiation source;

a pinion sharing a rotation shaft with the lower sprocket and rotatably provided to the intermediate member in a state in which a positional relationship thereof is fixed; and a rack meshed with the pinion and is provided to the support column so as to extend in a vertical direction, wherein an effective diameter of the lower sprocket is smaller than an effective diameter of the pinion.

2. The moving type radiation device as recited in claim 1, wherein the upper sprocket has the same effective diameter as an effective diameter of the lower sprocket.

3. The moving type radiation device as recited in claim 1, wherein the support column inner wire is multiplexed.

* * * * *